(12) United States Patent
Selic

(10) Patent No.: US 8,703,967 B2
(45) Date of Patent: Apr. 22, 2014

(54) CRYSTAL FORM OF SUNITINIB MALATE

(75) Inventor: Lovro Selic, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 138 days.

(21) Appl. No.: 13/128,580

(22) PCT Filed: Nov. 12, 2009

(86) PCT No.: PCT/EP2009/065030
§ 371 (c)(1),
(2), (4) Date: Jul. 7, 2011

(87) PCT Pub. No.: WO2010/055082
PCT Pub. Date: May 20, 2010

(65) Prior Publication Data
US 2011/0275690 A1    Nov. 10, 2011

(30) Foreign Application Priority Data

Nov. 13, 2008  (EP) .................................. 08169036

(51) Int. Cl.
*C07D 209/34* (2006.01)
(52) U.S. Cl.
USPC ........................................................ 548/468
(58) Field of Classification Search
CPC .................................................... C07D 209/34
USPC ........................................................ 548/468
See application file for complete search history.

(56) References Cited

FOREIGN PATENT DOCUMENTS

| WO | WO 01/60814 A2 | * | 8/2001 |
| WO | WO 03/016305 A1 | * | 2/2003 |
| WO | WO 03/016306 A1 | | 2/2003 |
| WO | WO-2009/067686 A2 | | 5/2009 |

OTHER PUBLICATIONS

Brittain H G, "Methods for the Characterization of Polymorphs and Solvates", Polymorphism in Pharmaceutical Solids, 1999, pp. 227-278.
Gadamasetti K., Braish T., "Process Chemistry in the Pharmaceutical Industry" vol. 2, Dec. 10, 2007, pp. 49-63.
Clas S-D et al., "Differential scanning calorimetry: Applications in drug development", Pharmaceutical Science and Technology Today Aug. 1, 1999 GB, vol. 2, No. 8, pp. 311-320.
Dong et al., "Synthesis of antitumor agent sunitinib malate" Chinese Journal of Medicinal Chemistry, vol. 18, No. 1, Feb. 1, 2008, pp. 28-31.
Vaidyanathan R Ed & Gadamasetti Kumar G et al; The Sutent Story; Passage Process Chemistry in the Pharmaceutical Industry; Challenges in an Ever Changing Climate; vol. 2, Jan. 1, 2007, pp. 49-64, XP008101878.

* cited by examiner

*Primary Examiner* — Shawquia Young
(74) *Attorney, Agent, or Firm* — Arent Fox LLP

(57) ABSTRACT

A process for the preparation of a new crystal form of sunitinib malate, along with pharmaceuticals comprising the same are described.

4 Claims, 3 Drawing Sheets

CRYSTAL FORM OF SUNITINIB MALATE

CROSS-REFERENCE TO RELATED APPLICATION

This is a 371 National Stage entry of International Application No. PCT/EP2009/065030, filed 12 Nov. 2009, now WO 2010/055082A2 published 20 May 2010, which claims benefit of priority to European Patent Application No. 08169036.4 filed 13 Nov. 2008, the entire contents of which are incorporated herewith in their entirety by reference.

FIELD OF THE INVENTION

The present invention relates to novel crystal form of sunitinib malate, to processes for its preparation and to pharmaceutical compositions containing it. The present invention also relates to improved process for preparing other crystal forms of sunitinib malate.

BACKGROUND OF THE INVENTION

The compound N-[2-(diethylamino)ethyl]-5-[-(5-fluoro-1,2-dihydro-2-oxo-3H-indol-3-ylidine)methyl]-2,4-dimethyl-1H-pyrrole-3-carboxamide, also named sunitinib (Formula I) has been shown to act as an inhibitor of protein kinases.

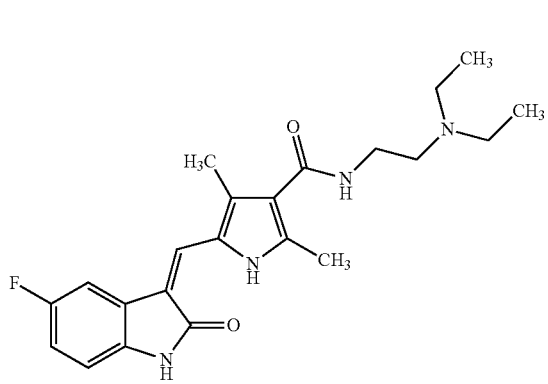

WO 01/60814 generally relates to pyrrole substituted 2-indolinone protein kinase inhibitors and includes sunitinib. In addition salts for the general class of compounds are generally referred to, such as positively charged moieties including quaternary ammonium, salts such as the hydrochloride, sulfate, carbonate, lactate, tartrate, malate, maleate, succinate; and negatively charged species. WO 01/60814 is silent as to the preparation of and the nature of specific crystal forms of salts.

In WO 03/016305 it is said that the free base and salts of sunitinib had been screened for properties related to the processing of the salt and the preparation of oral pharmaceutical compositions therefrom, including, for example, crystallinity, toxicity, hygroscopicity, stability, and morphology. Malate salt was chosen from the screening and two crystal forms of sunitinib L-malate, designated as Form I and Form II, were disclosed.

Polymorphism is defined as the ability of a substance to crystallize in more than one crystal lattice arrangement. Polymorphism can influence different aspects of solid state properties of a drug. Different crystal forms of a substance may differ considerably from one another in many respects such as their solubility, hygroscopicity, stability, solubility and/or dissolution rate, crystallinity, crystal habits, bioavailability and formulation handling characteristics.

The discovery of new polymorphic forms of a pharmaceutically useful compound provides a new opportunity to improve the performance characteristics of a pharmaceutical product.

Moreover, it would be desirable to provide a process for more selectively preparing a predetermined polymorphic form of sunitinib malate from among different theoretically existing polymorphic forms.

Thus, there is a need in the art for new polymorphic forms of sunitinib malate that have better thermal stability, and offer advantages for preparing reproducible pharmaceutical formulations. Further, there is a need to provide a predetermined polymorphic form in an aimed and reproducible manner, thereby allowing to obtain the desired specific, predetermined form in good purity.

The present invention satisfies this need by providing new crystal form comprising malic acid salt of sunitinib with greater thermodynamic stability, and by providing improved process for repeatedly obtaining a desired specific, predetermined form.

SUMMARY OF THE INVENTION

The present invention provides the following items including main aspects and preferred embodiments, which respectively alone and in combination particularly contribute to solving the above object and eventually provide additional advantages:

(1) Crystal form comprising malic acid salt of sunitinib, characterized by at least significant peaks at 2θ values of 5.7, 9.6, 17.8, 18.3 and 26.5 in an X-ray powder diffractogram, respectively exactly or ±0.2 degrees 2θ at the indicated 2θ values.

(2) Crystal form comprising malic acid salt of sunitinib, characterized by peaks at 2θ values of 5.7, 9.6, 11.5, 13.9, 17.8, 18.3, 19.3 and 26.5 in an X-ray powder diffractogram, respectively exactly or ±0.2 degrees 2θ at the indicated 2θ values.

(3) Crystal form comprising malic acid salt of sunitinib, characterized by an X-ray powder diffractogram shown in FIG. 1.

(4) Crystal form comprising malic acid salt of sunitinib, characterized by differential scanning calorimetry (DSC) thermogram having endotherm peak of at least about 218° C., particularly at 218° C.±5° C.

(5) Crystal form according to any one of preceding items, being essentially free of Form I and Form II.

(6) Crystal form according to any one of the preceding items, wherein the malic acid is L-malic acid.

(7) A process for the preparation of crystal form comprising malic acid salt of sunitinib, the process comprising the steps of:
  a.) mixing a compound of formula I, N-(2-(diethylamino)ethyl)-5-formyl-2,4-dimethyl-1H-pyrrole-3-carboxamide,

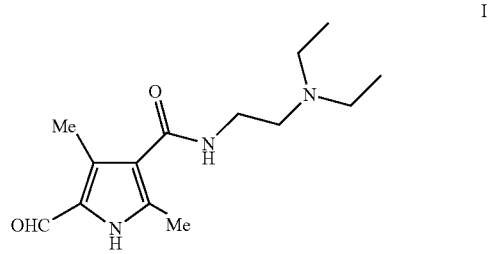 [SMILES: CCN(CC)CCNC(=O)c1c(C)[nH]c(C=O)c1C]

with compound of formula II, 5-fluoroindolin-2-one,

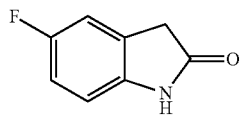

in a solvent;
b.) refluxing the mixture obtained in step a);
c.) adding malic acid to a mixture subsequent to step b); and
d.) allowing the crystal form comprising malic acid salt of sunitinib to crystallize subsequent to step c).

(8) The process according to item (7), wherein malic acid is L-malic acid.

(9) The process according to item (7) or (8), wherein steps a.) to d.) are carried out in one pot without intermediate isolation of sunitinib base formed by steps a.) and b.).

(10) The process according to any one of items (7) to (9), wherein sunitinib base and malic acid salt of sunitinib formed by steps a.) to c.) are respectively kept in solution until step d.) is started by cooling the solution obtained in step c).

(11) The process according to any one of items (7) to (10), wherein conditions, optionally including adjusting amounts of educts and/or reaction volume, are applied such that, until step d.) is started, the concentration of sunitinib does not exceed 25 mg/ml, preferably does not exceed 18 mg/ml and more preferably is adjusted to about 15 mg/ml. Optionally subsequently to said step c) and before step d) seeds of form III can be added. If the seeds are added, the concentration of sunitinib is preferably adjusted to about 25 mg/ml.

(12) The process according to any one of items (7) to (11), wherein step a.) is carried out in an organic solvent in the presence of organic base.

(13) The process according to item (12), wherein said organic solvent is selected form the group consisting of alcohol, acetonitrile, dialkyl ketone, N,N-dimethylformamide and mixtures thereof.

(14) The process according to item (13), wherein said organic solvent is lower alcohol, preferably ethanol.

(15) The process according to item (12), wherein said organic base is selected form the group consisting of linear amines, cyclic amines and alkoxides.

(16) The process according to item (15), wherein said organic base is pyrrolidine.

(17) The process according to any one of items (7) to (16), further comprising the step of isolation of said crystal form, preferably by filtration.

(18) The process according to any one of items (7) to (17), which is for preparing the crystal form according to any one of preceding items (1) to (6).

(19) A process for the preparation of a predetermined crystal form comprising malic acid salt of sunitinib from among at least two polymorphic forms, the process comprising the steps of:
(i) providing solid malic acid salt of sunitinib;
(ii) dissolving the solid malic acid salt of sunitinib in a solvent mixture comprising organic solvent and at least 5 vol.-% water;
(iii) allowing the predetermined crystal form comprising malic acid salt of sunitinib to crystallize.

(20) The process according to item (19), wherein the malic acid is L-malic acid.

(21) The process according to any one of items (19) and (20), wherein the malic acid salt of sunitinib in solution obtained in step (ii) is kept in solution until step (iii) is started by cooling the solution obtained in step ii).

(22) The process according to any one of items (19) to (21) for the preparation of crystal form I comprising malic acid salt of sunitinib, wherein the solid malic acid salt of sunitinib in step (ii) is dissolved in a mixture comprising acetonitrile and/or methanol and at least 5 vol.-% water, preferably about 5 to 20 vol.-% water.

(23) The process according to item (22), wherein the prepared crystal form I comprising malic acid salt of sunitinib has a melting point of 201-202° C.

(24) The process according to any one of items (19) to (21) for the preparation of crystal form II comprising malic acid salt of sunitinib, wherein step (iii) is performed while avoiding spontaneous crystallization, preferably involving freeze-drying. Avoiding spontaneous crystallization can be accomplished by performing no active induction of crystallization, e.g. not quickly but (if any) a carefully reducing the temperature of the mixture (especially if initial temperature of reaction mixture is elevated; however, careful cooling may not lead to spontaneous crystallization), not reducing the solution volume by evaporation (rather e.g. by freeze drying), not adding an antisolvent or not adding seeds.

(25) The process according to any one of items (19) to (21) and (24) for the preparation of crystal form II comprising malic acid salt of sunitinib wherein the solid malic acid salt of sunitinib in step (ii) is dissolved in a mixture comprising tetrahydrofuran and about 40 to 60 vol.-% water.

(26) The process according to any one of items (19) to (21), (24) and (25) for the preparation of crystal form II comprising malic acid salt of sunitinib, wherein in step (ii) the solid malic acid salt of sunitinib is dissolved at a concentration below 0.1 M, preferably below 0.05 M.

(27) The process according to any one of items (20) to (21) and (24) to (26), wherein the prepared crystal form II comprising malic acid salt of sunitinib has a melting point of 172-176° C.

(28) A pharmaceutical composition comprising the crystal form according to any one of items (1) to (6).

(29) A pharmaceutical composition obtained by: providing a crystal form prepared according to any one of items (7) to (17), and mixing the thus provided crystal form with one or more pharmaceutically acceptable excipients.

(30) A pharmaceutical composition obtained by: providing a pure crystal form I or II prepared according to any one of items (19) to (27), and mixing the thus provided crystal form with one or more pharmaceutically acceptable excipients.

(31) The pharmaceutical composition according to any one of items (28) to (30) for use in the prophylaxis or therapeutic treatment of a protein kinase related disorder in an organism, preferably wherein said protein kinase related disorder is a cancer selected from squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

DETAILED DESCRIPTION OF THE INVENTION

In the following, the present invention will be described in more detail by preferred embodiments and examples while referring to the attached drawings, noting, however, that these embodiments, examples and drawings are presented for illustrative purposes only and shall not limit the invention in any way.

Figure 5:
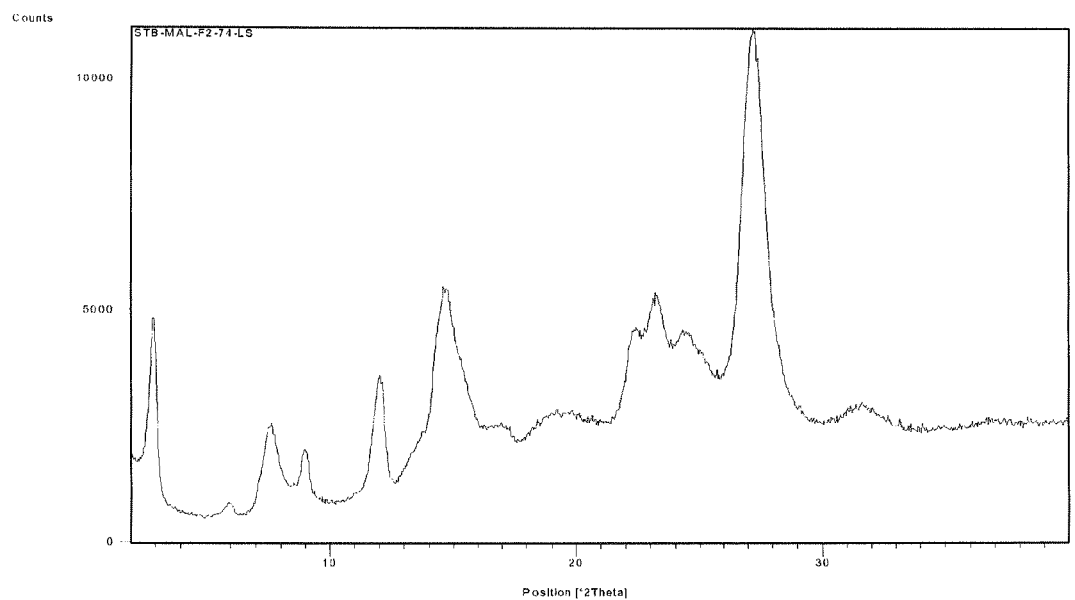
Figure 6:
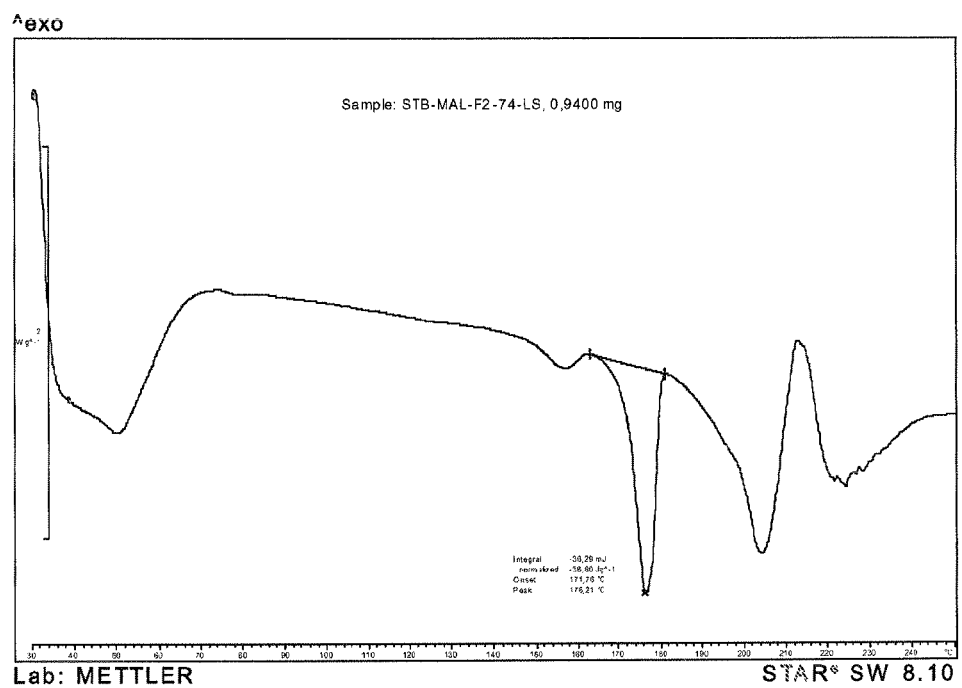

FIG. 5 is an X-Ray powder diffractogram of sunitinib L-malate Form II improved by an embodiment of the present invention; and FIG. 6 shows a DSC curve of the improved sunitinib L-malate Form II The term "about" used herein generally means within 10%, suitably within 5% and particularly within 1% of a given value or range. Alternatively, the term "about" means within an acceptable standard error of the mean, when considered by one of the ordinary skill in the art.

According to one aspect, the present invention discloses novel crystal form comprising malic acid salt of sunitinib, designated Form III.

Form III according to present invention has great thermodynamic stability which is indicative for improved chemical and/or physical stability, shows no changes in polymorphic form and has a high degree of crystallinity.

Present invention also provides a simple, effective and economically advantageous process for preparation of crystal form III of sunitinib malate, where formation of sunitinib and formation of its malate salt form part of the same process.

Furthermore crystal form III of sunitinib malate, once formed, is easy to purify and due to its excellent stability easy to handle.

Unexpectedly, the crystal form comprising malic acid salt of sunitinib (Form III) according to the present invention, compared with previously described Forms I and II, is thermodynamically more stable and thus is likely to display higher chemical and/or physical stability.

Malic acid salt may be a salt of D-malic acid, D,L-malic acid, L-malic acid or combinations thereof. Preferably, malic acid salt is a salt of L-malic acid.

Figure 1:
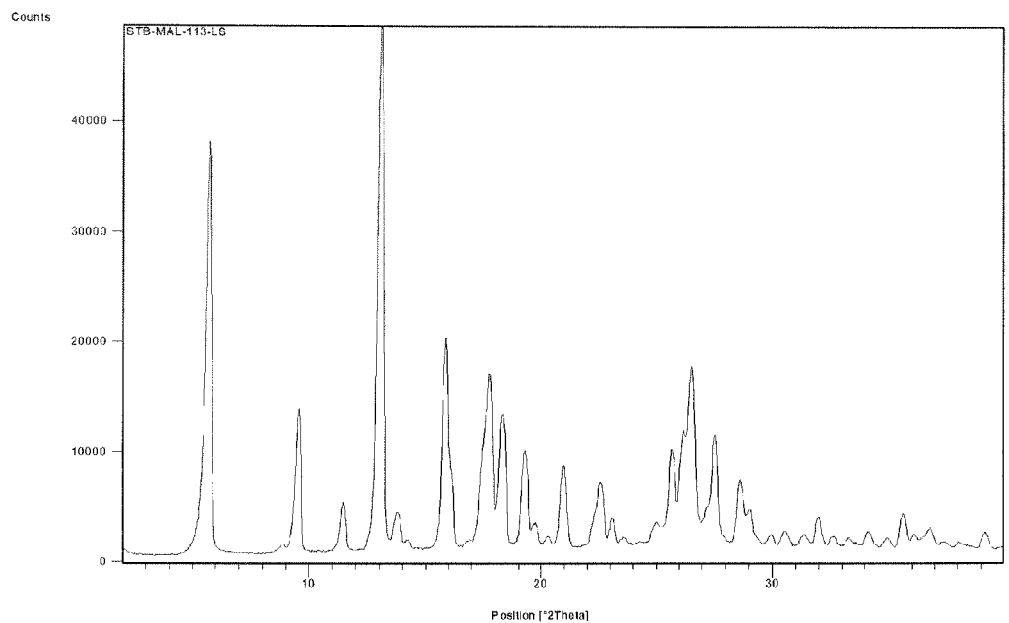
FIG. 1 is an X-Ray powder diffractogram of sunitinib L-malate Form III according to a preferred embodiment of the present invention.

In certain embodiments, the present invention relates to crystal Form III of sunitinib malate, characterized by one of the following particular X-ray powder diffractogram patterns:

in a sufficiently pure and unique form, the crystal form comprising malic acid salt of sunitinib is characterized by at least significant peaks at 2θ values of 5.7, 9.6, 17.8, 18.3 and 26.5 in an X-ray powder diffractogram, respectively exactly or ±0.2 degrees 2θ at the indicated 2θ values;

in a more pure and specific form, the crystal form comprising malic acid salt of sunitinib is characterized by peaks at 2θ values of 5.7, 9.6, 11.5, 13.9, 17.8, 18.3, 19.3 and 26.5 in an X-ray powder diffractogram, respectively exactly or ±0.2 degrees 2θ at the indicated 2θ values; and in a certain exemplified form, the crystal form comprising malic acid salt of sunitinib is characterized by an X-ray powder diffractogram shown in FIG. 1.

In another aspect invention relates to a crystal form comprising malic acid salt of sunitinib characterized by differential scanning calorimetry (DSC) thermogram having endotherm peak of at least about 218° C., particularly 218° C.±5° C. Surprisingly, the teaching disclosed herein allows to obtain pure sunitinib malate with melting points substantially higher than previously known, which is indicative for yielding high thermodynamic and thus chemical and/or physical stability. A specifically exemplified sunitinib malate satisfying this purity and stability is crystal Form III disclosed herein.

Another aspect of the present invention relates to a process for the preparation of crystal form comprising malic acid salt of sunitinib, the process comprising the steps of:

a) mixing a compound of formula I, N-(2-(diethylamino)ethyl)-5-formyl-2,4-dimethyl-1H-pyrrole-3-carboxamide

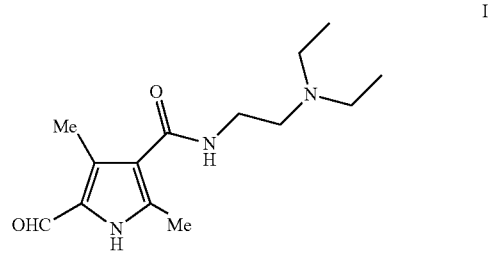 [SMILES: CCN(CC)CCNC(=O)c1c(C)[nH]c(C=O)c1C]

with compound of formula II, 5-fluoroindolin-2-one

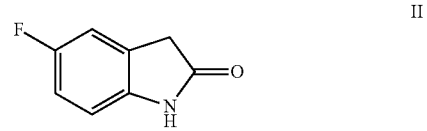 [SMILES: O=C1Cc2cc(F)ccc2N1]

in a solvent b) refluxing the mixture obtained in step a);

c) adding malic acid to a mixture subsequent to step b); and d) allowing the crystal form comprising malic acid salt of sunitinib to crystallize subsequent to step c).

This aspect of the present invention provides particularly efficient combination of process steps to repeatedly arrive at pure and physically stable Form III of sunitinib malate. Formation of sunitinib and formation of its malate salt according to this aspect of the present invention constitute parts of a common process, i.e. involving consecutive steps which start from relevant educts and finally yield the desired malic acid salt of sunitinib. The process is economically advantageous and allows the desired salt to be easily and repeatedly purified. It can be beneficially performable in one-pot, without intermediate isolation of sunitinib base formed by steps a.) and b.) being necessary.

Surprisingly, it has been found that the process according to the afore-defined aspect of the present invention allows to keep both the sunitinib base formed from steps a) and b) and the malic acid salt of sunitinib formed from step c) respectively in solution until step d.) is started, for example by cooling the mixture obtained in step c). Maintaining the sunitinibe base produced in partial step a) in solution, which is assisted by suitable means, including but not limited to e.g. choosing an appropriate solvent, adjusting an appropriate sunitinib compound concentration in solution, keeping the mixture at the boiling point of the liquid medium put under reflux, and adding malic acid to this mixture preferably at an elevated temperature and more preferably at the boiling point of the liquid medium but suitably still at a lower temperature down to room temperature, has been found significant to yield, in the crystallization step d), Form III of sunitinib malate in stable and pure form.

Compound of formula I is mixed with and reacted with the compound of formula II in suitable solvent, preferably in an organic solvent and more preferably in the presence of organic base to form sunitinib. Organic solvent is preferably selected form the group consisting of alcohol, acetonitrile, dialkyl ketone, acetonitrile, formamide and mixtures thereof. Most preferably organic solvent is ethanol. Its relatively high boiling point is advantageous for the reaction to take place rapidly, and in combination therewith it provides for dissolution of sunitinib.

Optionally subsequently to step c) and before step d) seeds of form III can be added. The desired concentration is preferably about 5-25 mg/ml, more preferably about 12-18 mg/ml, most preferably about 15 mg/ml of hypothetically formed sunitinib in order to prevent the precipitation of sunitinib out of solution in this stage of process, i.e. before malate salt is formed or the formed salt is precipitated or crystallized in a premature state. If the process is performed with the addition of seeds, the concentration of sunitinib is preferably adjusted to about 25 mg/ml.

Appropriate conditions can be chosen to adjust such beneficial concentration of sunitinib base formed, including but not limited to using correspondingly calculated amounts of educts for the reaction step a), volume of the reaction medium, and the like.

Suitable organic base is selected form the group consisting of linear amines, such as for example monoalkyl, dialkyl and trialkyl amines, cyclic amines, such as for example pyrrolidine, and alkoxides. Most preferably organic base is pyrrolidine.

A molar ratio of compound of formula I to compound II is preferably about 1:1.

The reaction mixture is refluxed, preferably for about 0.5-5 hours, more preferably about 1.5 hours. Subsequently malic acid and preferably its L-isomer is added, preferably in about equimolar ratio to compounds of formula I and II or an excess of the acid is used.

Form III of sunitinib can be isolated or recovered from the reaction solution by precipitation, while allowing the desired crystal form to crystallize. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water, ethers and hydrocarbons.

In one aspect of the invention the precipitation of form III of sunitinib occurs after long standing the solution at appropriate temperature below 50° C., preferably between −10 to 30° C., most preferably at room temperature at about 19 to 25° C., while optionally stirring, after cooling optionally stirred mixture from heated solution below 50° C., preferably to room temperature or bellow, both after optional concentration of the solution by partial evaporation of solvents.

In another option form III of sunitinib is formed by precipitation adding antisolvent preferably selected from water, ethers and hydrocarbons.

Obtained crystals of form III sunitinib may be separated by techniques well known in the art, e.g. filtration, centrifugation, decanting. Preferably filtration is used.

In another aspect the present invention relates to a process for preparation of pure and predetermined forms of sunitinib malate and especially of sunitinib L-malate, including the preparation of predetermined conventional form II and form I, respectively. In common, it was found significant that a proper dissolution of malic acid salt of sunitinib is made, and a precipitation in a stage too early and premature is carefully controlled and beneficially avoided. Interestingly, specific conditions have been found which are tailored to prepare, according to the desire, a predetermined crystal form of sunitinib malate from among the various theoretically existing polymorphic forms. While for the specific preparation of both forms I and II according to this aspect of the present invention, it is the common concept to first provide solid malic acid salt of sunitinib and to dissolve the solid malic acid salt of sunitinib, as raw material, in a solvent mixture comprising organic solvent and at least 5 vol.-% water prior to start of a re-crystallization step, it is significant that a complete dissolution of the solid malic acid salt of sunitinib is realized and the subsequent critical conditions are correspondingly adapted, including one or more of: (i) selection of specifically adapted solvent system which requires certain amount of water, (ii) adjusting the appropriate proportion of water in the solvent system, (iii) avoiding spontaneous solvent evaporation and thus spontaneous precipitation (iv) adjusting a respectively adapted temperature of the solvent system for both during dissolution and thereafter, and (v) adjusting a correspondingly adapted concentration of sunitinibe malate in solution, especially from fairly diluted to highly diluted samples. In this manner, it was feasible to obtain Form I and Form II of sunitinibe L-malate repeatedly in well-aimed manner in high purity and high stability previously not anticipated. High purity preferably means substantially only the predetermined, desired crystal form, i.e. either form I or form II, and substantially no amount of the respective other form. Since the achievement of the desired form can be predetermined by this aspect of the present invention, a practically unresolvable complex mixture of both forms I and II can be surely avoided. Freeness from the respective other form according to the present invention can be determined by being essentially undetected, and even practically undetected, in X-ray diffraction spectra evaluated.

In a specific embodiment the predetermined crystal form is form II, and particularly it relates to a process for preparation of pure and highly crystalline form II of sunitinib L-malate. In one preferred example diluted solution of sunitinib malate in mixture of organic solvent and water, preferably THF and water, using at least 5 vol.-% and preferably about 40 to 60 volume percentage of water, more preferably about 55 volume percentage of water. Preferred concentration of said diluted solution is below 0.1 M, more preferably below 0.05 M.

It has been found effective to start with dissolving sunitinib malate in the water component of the solvent system first, in order to get more complete dissolution without necessarily heating the liquid, before the organic solvent component is added. If necessary, said diluted solution may be heated until sunitinib malate is completely dissolved, then carefully cooled, preferably to about room temperature, to avoid spontaneous crystallization. For the sake of obtaining more pure and stable form II salt, it has been found effective to then freeze dry the solution, suitably at a temperature below about −10° C., preferably at about −20° C. This embodiment does not use evaporation and avoids spontaneous crystallization.

Obtained crystals of form II may be separated by techniques well known in the art, e.g. filtration, centrifugation, decanting.

Crystalline form II of sunitinib prepared according to such procedure exhibits melting point at about 172-176° C.

In another specific embodiment the predetermined crystal form is form I, and particularly it relates to a process for preparation of pure and highly crystalline form I of sunitinib L-malate. In one preferred example raw sunitinib malate is suspended in mixture of organic solvent and water, preferably acetonitrile or methanol and water, more preferably methanol and water, using at least 5 vol.-% and preferably about 5 to 20 volume percentage of water, more preferably about 10 volume percentage of water. Said mixture may be heated until sunitinib malate is dissolved.

Form I of sunitinib can be isolated or recovered from the reaction solution by precipitation. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water, ethers and hydrocarbons.

In one aspect of the invention the precipitation of form I of sunitinib occurs when said heated mixture is left to cool, preferably to room temperature, to give crystals of pure form I.

Obtained crystals of form I may be separated by techniques well known in the art, e.g. filtration, centrifugation, decanting.

Crystalline form I of sunitinib prepared according to such procedure exhibits melting point at about 201-202° C.

Another aspect of the present invention is a pharmaceutical composition for administering a therapeutically effective amount of crystal form III of sunitinib malate of present invention in unit dosage form with one or more pharmaceutically acceptable carriers or other excipients.

A therapeutically effective amount of crystal form III of sunitinib malate of the present invention is, when calculated as sunitinib base, from 5 to 150 mg, preferably from 10 to 100 mg, more preferably from 10 to 50 mg.

Crystal form III of sunitinib malate in accordance with present invention can be embodied for example in form of tablet, capsules, pellets, granules and suppositories or their combined forms. Pharmaceutical composition in accordance with present invention can be suitable for immediate release or modified release of crystal form III of sunitinib malate of the present invention. Solid pharmaceutical compositions can be for example coated with aim of increasing peletibility or regulating the disintegration or absorption.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of lactose, microcrystalline cellulose, cellulose derivatives, (e.g. hydroxypropylcellulose, croscarmellose sodium), polyacrylates, calcium carbonate, starch, colloidal silicone dioxide, sodium starch glycolate, talc, magnesium stearate, mannitol, polyvinylpyrrolidone, polyethylene glycol and other excipients known in the field of the pharmaceutical technology.

Optionally, the pharmaceutical compositions of the invention may be combination product comprising one or more additional pharmaceutically active components in addition to crystal form III of sunitinib malate.

The pharmaceutical compositions according to the present invention may be prepared by methods known in the field of the pharmaceutical technology.

The further aspect of the present invention is a method for treatment of a protein kinase related disorder in an organism, with a medicament by using an effective amount of crystal form III of sunitinib malate according to the present invention.

In another aspect the present invention is related to use of crystal form III of sunitinib malate, for the manufacture of medicament for treatment of a protein kinase related disorder in an organism.

Said protein kinase related disorder is preferably a cancer selected from squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

According to another aspect, a pharmaceutical composition according to the invention can be obtained by providing a crystal form prepared according to any one of the above disclosed processes for yielding stable and pure sunitinib malate forms, notably either one of sunitinib L-malate forms I, II and III respectively, and mixing the thus provided crystal form with one or more pharmaceutically acceptable excipients. Freeness from other forms needs to be observed already at the stage of preparing and isolating the respectively predetermined form, and is significant to eventually obtain reproducible pharmaceutical compositions without variations with respect to stability and dissolution profiles. The descriptions above on form III with respect to therapeutically effective amount, dosage forms, excipients, therapeutic treatments, and combinations with other active pharmaceutical ingredients, apply with respect to such other forms I and II correspondingly.

EXPERIMENTAL PROCEDURES

Raw sunitinib malate may be prepared based on descriptions in WO 01/60814.

Comparative Example

According to WO 03/016305, form I sunitinib malate was prepared. Essentially, poorly crystalline raw material was suspended in acetonitrile and the suspension was heated. After cooling, the thus produced material had a m.p. of 196-198° C.

On the other hand, form II sunitinib malate was prepared by dissolving raw material in a mixture of THF and water, followed by spontaneous evaporation.

As a result complex mixtures of forms, including form I and predominantly form II, were isolated in attempts to reproduce experiments of WO 03/016305.

Example 1

0.6 g of raw sunitinib malate containing a mixture of various forms as well as other unidentified forms was suspended in 7.5 ml of mixture of methanol and water 10/1 and heated until all material was dissolved, then left to cool to room temperature to give crystals of pure form I. Melting point: 201-202° C.

Figure 3:
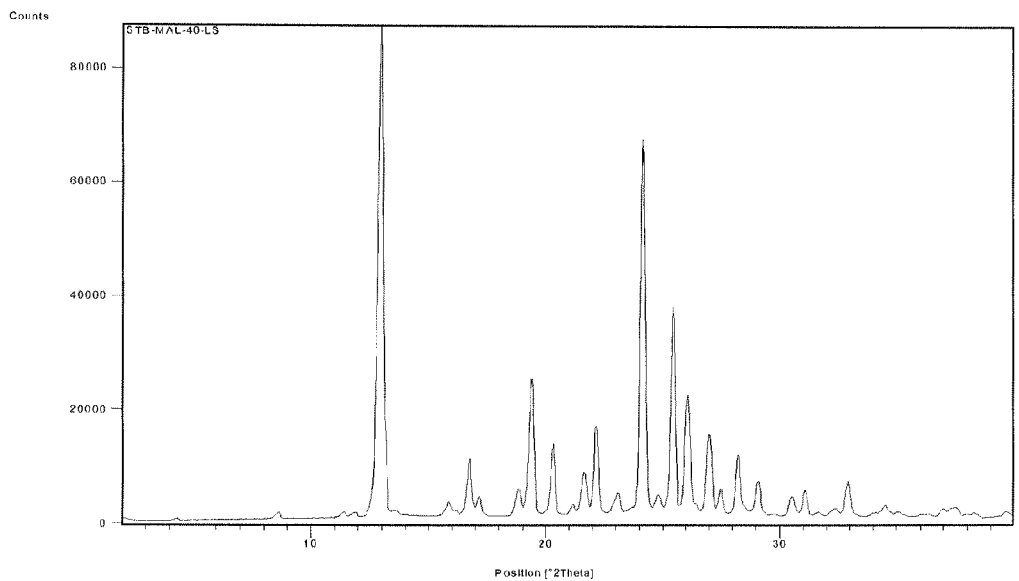
FIG. 3 is an X-Ray powder diffractogram of sunitinib L-malate Form I improved by an embodiment of the present invention.
Figure 4:
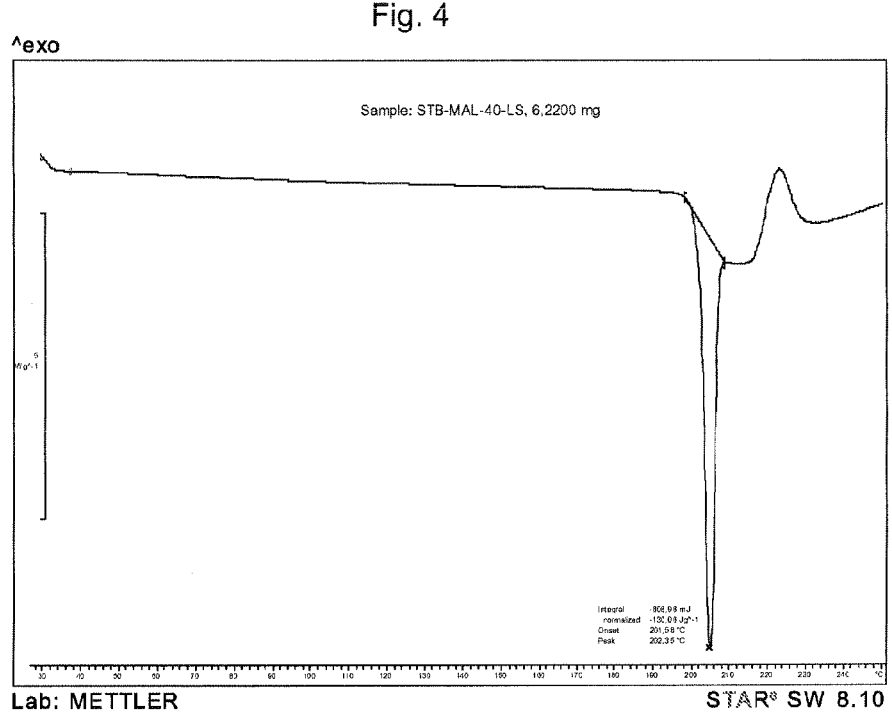
FIG. 4 shows a DSC curve of the improved sunitinib L-malate Form I

An XRD of the resulting sunitinib L-malate Form I is shown in FIG. 3, and a DSC curve thereof is shown in FIG. 4.

Example 2

0.47 g of sunitinib malate was dissolved in water (20 ml), 25 ml of THF was added to give fairly diluted complete solution and then carefully cooled to avoid spontaneous crystallization. The prepared solution was freeze dried at −20° C. The recovered fluffy material is pure form II. Melting point: 172-176° C.

An XRD of the resulting sunitinib L-malate Form II is shown in FIG. 5, and a DSC curve thereof is shown in FIG. 6.

Example 3

A one-pot, combined synthesis and formation of a crystal form comprising malic acid salt of sunitinib as shown in the following scheme was carried out.

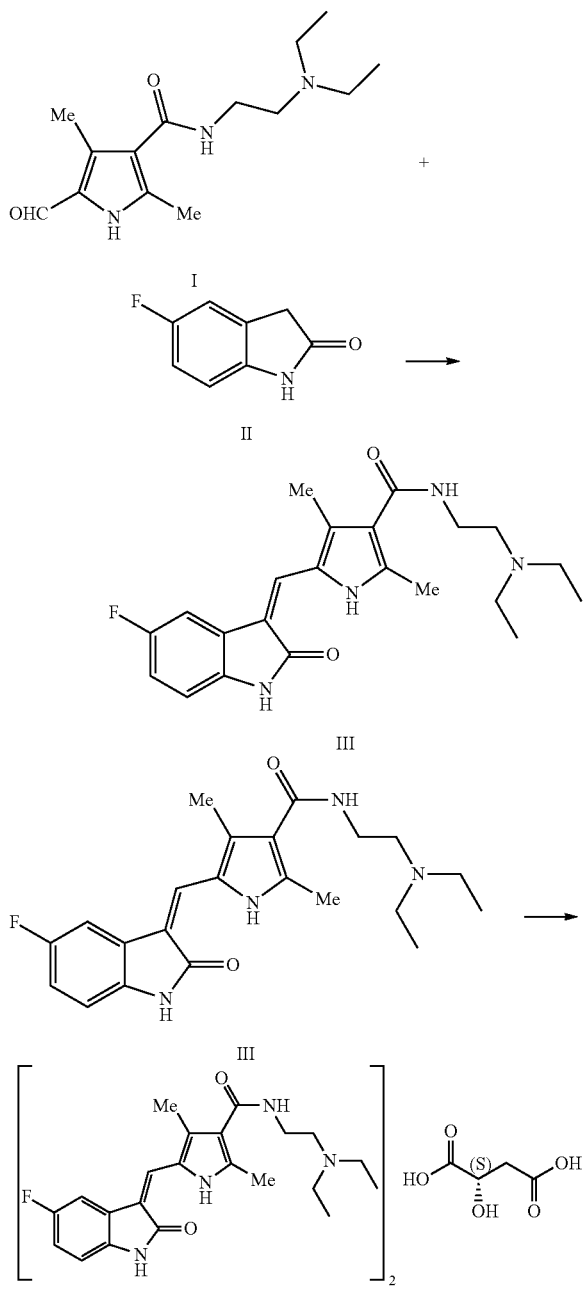

To a solution of 1.40 g (5.28 mmol) N-(2-(diethylamino)ethyl)-5-formyl-2,4-dimethyl-1H-pyrrole-3-carboxamide (I) and 0.76 g (5.03 mmol) 5-fluoroindolin-2-one (II) in ethanol (140 ml), 0.023 ml of pyrrolidine was added and mixture was refluxed for 1.5 h. After that, 0.71 g of L-malic acid was added and mixture left to cool to room temperature and stirred for few hours until all precipitate was formed. Crystals were collected by filtration to give 2.07 g (84%) of the novel form, defined above as sunitinib malate form III. Melting point: 217-219° C.

Figure 2:
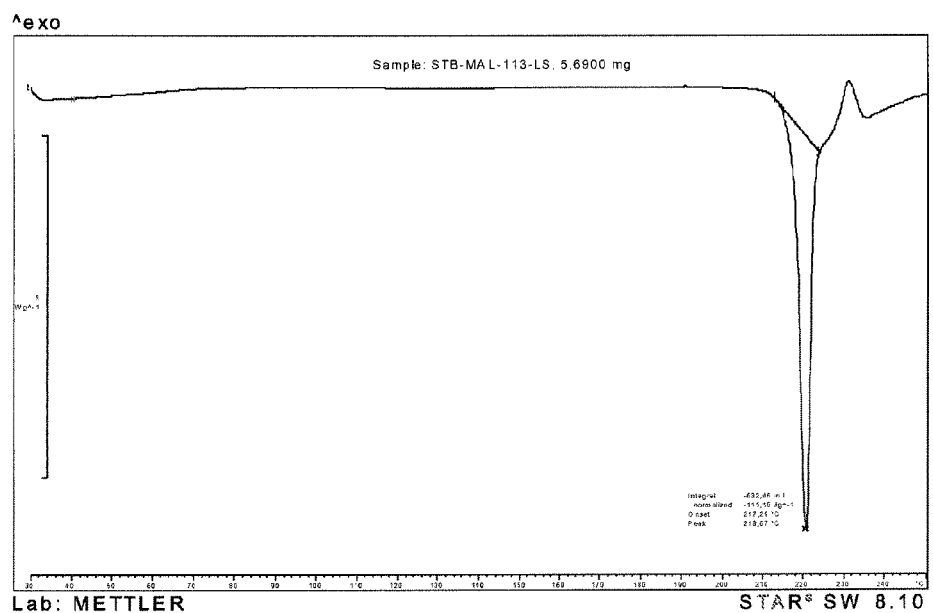
FIG. 2 shows a DSC curve of sunitinib L-malate Form III according to a preferred embodiment of the present invention.

An XRD of the resulting sunitinib L-malate Form III is shown in FIG. 1, and a DSC curve thereof is shown in FIG. 2.

Example 4

To a solution of 6.63 g (25 mmol) N-(2-(diethylamino)ethyl)-5-formyl-2,4-dimethyl-1H-pyrrole-3-carboxamide (I) and 3.78 g (25 mmol) 5-fluoroindolin-2-one (II) in ethanol (400 ml), 0.25 ml of pyrrolidine was added and mixture was refluxed for 5 h. To a boiling reaction mixture, a solution of malic acid (1.77 g, 12.5 mmol) in ethanol (10 ml) was added and a seed (50 mg); (obtained from example 3) is added and a solution is left to cool to ambient temperature, with slow (as slow as possible) stirring. The mixture is left to stir for another 16 hours, then the product is filtered (9.77 g, 84%).

Methods of Analysis

The products were analyzed by following methods:

X-Ray Powder Diffraction Method:

Conditions for obtaining powder X-ray diffraction (XRD) patterns: The powder X-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40°2θ in steps of 0.033°2θ and the measurement time of 50 seconds per step. Variable divergence and antiscatter slits were used to maintain 12 mm of sample length irradiated.

Differential Scanning Calorimetry:

Conditions for obtaining DSC thermograms: Thermograms were obtained with Mettler Toledo DSC822e differential scanning calorimeter. The sample (4-6 mg) was placed in an unsealed aluminium pan with a hole and heated at 5° C./min in the temperature range from 30° C. to 250° C.

The invention claimed is:

1. A process for the preparation of crystal form comprising malic acid salt of sunitinib, the process comprising the steps of:
  a) mixing a compound of formula I, N-(2-(diethylamino)ethyl)-5-formyl-2,4-dimethyl-1H-pyrrole-3-carboxamide

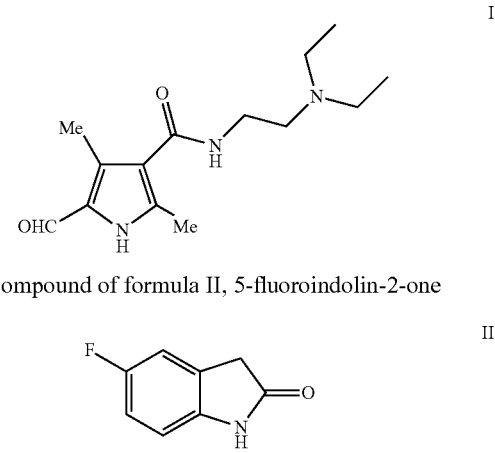

with compound of formula II, 5-fluoroindolin-2-one in a solvent;
  b) refluxing the mixture obtained in step a);
  c) adding malic acid to a mixture subsequent to step b); and
  d) allowing the crystal form comprising malic acid salt of sunitinib to crystallize subsequent to step c), wherein steps a) to d) are carried out in one pot without intermediate isolation of sunitinib base formed by steps a) and b).

2. The process according to claim 1, wherein malic acid is L-malic acid.

3. The process according to claim 1, wherein step a) is carried out in an organic solvent in the presence of organic base.

4. The process according to claim 1, wherein conditions, optionally including adjusting amounts of educts and/or reaction volume, are applied such that, until step d) is started, the concentration of sunitinib does not exceed 25 mg/ml.

* * * * *